United States Patent [19]
McAllister

[11] Patent Number: 5,454,384
[45] Date of Patent: Oct. 3, 1995

[54] SKIN-TIGHTENING METHOD

[76] Inventor: David R. McAllister, 36 Skyline Dr., Lake Mary, Fla. 32746

[21] Appl. No.: 305,021

[22] Filed: Sep. 13, 1994

[51] Int. Cl.⁶ .................................................. A61B 19/00
[52] U.S. Cl. ...................... 128/898; 606/167; 606/204.35
[58] Field of Search ..................................... 128/898, 897; 606/1, 9, 131, 132, 204.35, 204, 213, 214, 216, 167

[56] References Cited

U.S. PATENT DOCUMENTS

| | | | |
|---|---|---|---|
| 3,911,909 | 10/1975 | Di Matteo | 128/76 B |
| 3,949,741 | 4/1976 | Hofmann | 128/76 B |
| 5,370,642 | 12/1994 | Keller | 128/898 |

Primary Examiner—Stephen C. Pellegrino
Assistant Examiner—Glenn Dawson
Attorney, Agent, or Firm—Allen, Dyer, Doppelt, Franjola & Milbrath

[57] ABSTRACT

A noninvasive skin-tightening method is provided wherein a target line or wrinkle is selected that the patient wishes to minimize or eradicate. A pair of lines is scratched in the skin parallel to and one on each side of the target line. Preferably two series of lines are then scratched in the skin, one series parallel to each of the first pair of lines, with a separation of at least ¹⁄₁₆ inch. The post-treatment steps include cleaning the scratches with antibacterial soap, drying the area, and massaging with antibacterial topical cream. Once the lines scratched in the skin are permitted to heal, the skin is found to be tightened.

12 Claims, 2 Drawing Sheets

SKIN-TIGHTENING METHOD

BACKGROUND OF THE INVENTION

1. Field of the Invention

The present invention relates to skin treatment methods, and, more particularly, to removing wrinkles from the skin.

2. Description of Related Art

Several techniques for providing a more youthful appearance-to the skin are known in the art. The most invasive of these is plastic surgery, such as face lifts, to tighten the skin by (greatly simplified) making an incision in the skin, pulling it tight, cutting off a flap of skin, and suturing the two ends of the skin together.

A laser technique has also been disclosed, sometimes referred to as "laser acupuncture." In this method radiation from a helium-neon laser is directed to wrinkled areas, which are claimed to be smoothed out thereby.

Dermabrasion and chemical peels are known in the art, both of which remove an epidermal layer of skin, leaving behind a smoother, more youthful-looking layer.

A facial wrinkle remover has been disclosed by Di Matteo (U.S. Pat. No. 3,911,909). The device comprises an element for applying pressure to the interior surface of the mouth and another element for applying pressure to the exterior surface of the face, the two elements connected together.

The wrinkle-reducing method of Hofmann (U.S. Pat. No. 3,949,741) teaches the use of a pressure-sensitive adhesive film that is applied to the skin, left on for at least four hours, and stripped off, removing with it a layer of dead cells.

SUMMARY OF THE INVENTION

It is an object of the present invention to provide an incision-free, noninvasive, inexpensive, painless skin-tightening method.

It is a further object to provide such a method that does not require the use of radiation.

It is an additional object to provide such a method that does not require the removal of a layer of skin.

The method of the present invention that satisfies the above-listed objects is a noninvasive method of tightening the skin of a patient. The method comprises the steps of selecting a target line in the skin of the patient around which the patient wishes to achieve tightening. Such a target line may comprise a wrinkle on the face or elsewhere on the body.

Next, using a sharp, sterile tool such as a razor or scalpel, a first line is scratched in the skin parallel to and on a first side of the target line. A second line is then scratched in the skin parallel to and on a second side of the target line. The lines scratched in the skin are then permitted to heal, during which the skin is tightened.

In a preferred embodiment, following the scratching steps, the scratched lines are massaged with an antibacterial preparation. Also in a preferred embodiment, the scratched lines are carefully cleaned prior to the scratching steps.

In an alternate embodiment, a first series of additional lines are scratched in the skin parallel to the first line, wherein the first line is between the target line and the additional lines. Similarly, a second series of additional lines are scratched in the skin parallel to the second line, wherein the second line is between the target line and the additional lines. For both the first and the second series of additional lines, each line is at least 1/16 inch from a neighboring line.

In a preferred embodiment, a skin scratching tool is also provided. The tool comprises a handle having a first end and a second end and a pair of spaced-apart support members. Each support member is affixed at a first end adjacent and generally perpendicular to the second end of the handle. In addition, the tool comprises a plurality of blades affixed to, spanning, and generally perpendicular to the support members. The blades each have a sharp side, the sharp sides facing a same direction. In addition, the blades are spaced apart from each other at a predetermined separation distance.

In use the first end of the scratching tool is held by the operator and is used to scratch a first series of lines in the skin parallel to and on a first side of the target line. The tool thereby permits a parallel series of lines to be scratched having the predetermined separation and a guaranteed degree of parallelism. Then a second series of lines is scratched in the skin parallel to and on a second side of the target line using the scratching tool.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE PREFERRED EMBODIMENT

Figure 1:
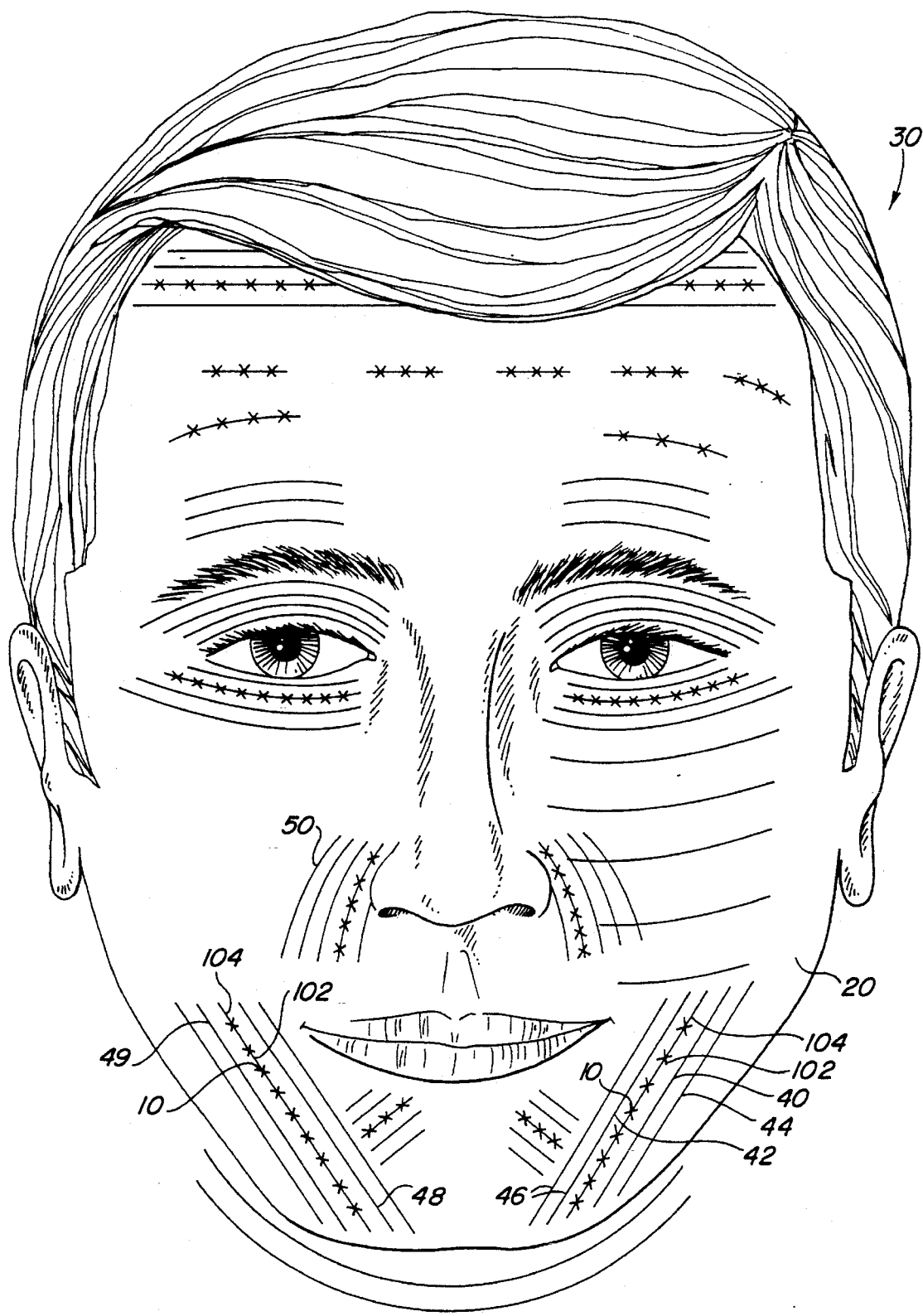
FIG. 1 illustrates target lines on the face of a patient and lines scratched in the skin around the target lines for the purpose of tightening those areas.
Figure 2:
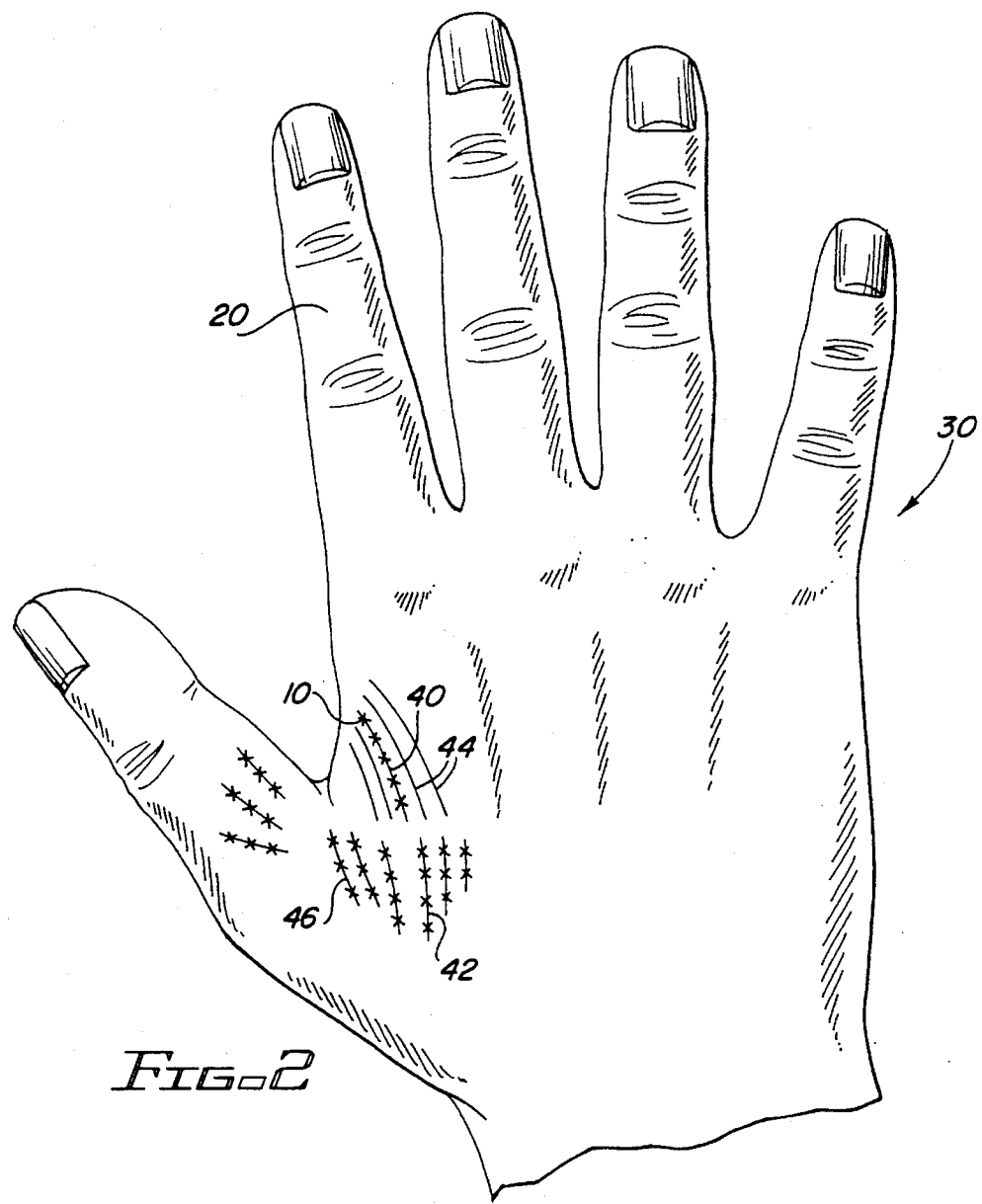
FIG. 2 depicts the method of the present invention utilized on a hand.
Figure 3A:
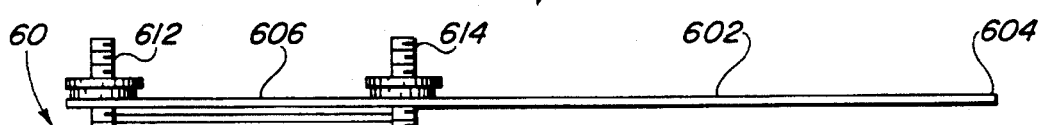
FIG. 3 illustrates the scratching tool of the present invention. (a) is a plan view; (b), a side view.
Figure 3B:
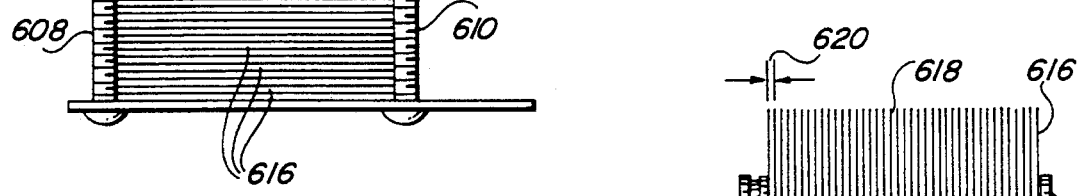

A description of the preferred embodiments of the present invention will now be presented with reference to FIGS. 1–3.

The noninvasive method of the present invention, for tightening the skin of a patient, comprises the steps of selecting a target line 10 in the skin 20 of the patient 30.

In FIG. 1 is shown the method applied to the face; in FIG. 2, to the hand. The skin to be worked on should be cleaned with antibacterial soap, and all tools used should be sterilized.

A first line 40 is scratched in the skin 20 parallel to and on a first side 102 of the target line 10, and a second line 42 is scratched in the skin 20 parallel to and on a second side 104 of the target line 10. The scratches may be made with a sterilized razor or a scalpel, the blade of which must be extremely sharp so that it glides across the skin without drawing blood.

Next the scratched lines 40 and 42 are cleaned with antibacterial soap, dried, and massaged with an antibacterial preparation 50 to prevent infection. Preparation 50 comprises, in a preferred embodiment, a topical cream comprising neomycin and polymyxin B, such as that marketed under the brand name Neosporin®. The massaging is best done in small, circular strokes.

Finally the scratches 40 and 42 are permitted to heal, during which the skin is tightened. Typically there is some swelling following treatment, most of which dissipates within 24 hours after treatment. Any remaining red lines are generally eradicated within 48 hours. Additional treatments on other target lines may 10 be undertaken a week later.

In a preferred embodiment, a first series of additional lines 44 is scratched in the skin 20 parallel to the first line 40, wherein the first line 40 is between the target line 10 and the additional lines 44. Each line is recommended to be placed at least 1/16 inch from a neighboring line. Similarly, a second series of additional lines 46 is scratched in the skin 20 parallel to the second line 42, wherein the second line is between the target line 10 and the additional lines 46. Again, each line is recommended to be placed at least 1/16 inch from a neighboring line. It is again preferred that the steps of cleaning, drying, and massaging with topical antibacterial preparation are taken to aid in the healing process and prevent infection.

Preferably the first 44 and second series 46 of lines should have an equal number and should be roughly equal in length.

Two further embodiments of the method of the present invention comprise: (1) drawing guide lines on the skin around the target line prior to the scratching steps; and (2) projecting a guide line grid onto the skin using, for instance, an overhead projector, also prior to the scratching steps. These preparatory steps will aid in placing the scratches more accurately.

In FIG. 3 is illustrated a tool that is provided to assist in making uniform, parallel, scratches in the skin that are spaced apart at a predetermined distance. The skin scratching tool 60 of the present invention comprises a handle 602 having a first end 604 and a second end 606. A pair of spaced-apart support members 608 and 610 is affixed at their first ends 612 and 614, respectively, adjacent and generally perpendicular to the second end 606 of the handle 602.

Tool 60 further comprises a plurality of spaced-apart generally parallel blades 616 affixed to, spanning, and generally perpendicular to the support members 608 and 610. The blades 616 each have a sharp side 618, and the sharp sides 618 all face in the same direction. The blades 616 further have a predetermined separation 620 between adjacent blades 616, in the embodiment shown 1/16 inch.

As in the previously described embodiment, a target line 10 in the skin 20 of the patient 30 is selected. The operator, holding the first end 604 of the handle 602 of the scratching tool, scratches a first series of lines 48 in the skin 20 parallel to and on a first side 102 of the target line 10 using the scratching tool 60. Then a second series of lines 49 is scratched in the skin 20 parallel to and on a second side 104 of the target line 10 using the scratching tool 60.

As previously, the scratched lines 48 and 49 are cleaned with antibacterial soap and dried. Next the lines 48 and 49 are massaged with an antibacterial preparation, a topical cream comprising neomycin and polymyxin B. As above, the scratches 48 and 49 in the skin 20 are permitted to heal, during which the skin 20 is tightened.

It may be appreciated by one skilled in the art that additional embodiments may be contemplated, including tightening the skin on other portions of the body.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the method illustrated and described herein are by way of example, and the scope of the invention is not limited to the exact details of the method.

Having now described the invention, and the operation and use of preferred embodiments thereof, and the advantageous new and useful results obtained thereby, the new and useful steps thereof obvious to those skilled in the art, are set forth in the appended claims.

What is claimed is:

1. A noninvasive method of tightening the skin of a patient, the method comprising the steps of:

selecting a target line in the skin of the patient;

scratching a first line in the skin parallel to and on a first side of the target line;

scratching a second line in the skin parallel to and on a second side of the target line; and permitting the lines scratched in the skin to heal, during which the skin is tightened.

2. The method recited in claim 1, further comprising the step, following the scratching steps, of massaging the scratched lines with an antibacterial preparation.

3. The method recited in claim 2, wherein the antibacterial preparation comprises a topical cream comprising neomycin and polymyxin B.

4. The method recited in claim 2, further comprising the step, prior to the massaging step, of cleaning the scratched lines.

5. A noninvasive method of tightening the skin of a patient, the method comprising the steps of:

selecting a target line in the skin of the patient;

scratching a first line in the skin parallel to and on a first side of the target line;

scratching a first series of additional lines in the skin parallel to the first line, wherein the first line is between the target line and the additional lines, each line at least 1/16 inch from a neighboring line;

scratching a second line in the skin parallel to and on a second side of the target line;

scratching a second series of additional lines in the skin parallel to the second line, wherein the second line is between the target line and the second series of additional lines, each line at least 1/16 inch from a neighboring line; and permitting the scratches in the skin to heal, during which the skin is tightened.

6. The method recited in claim 5, further comprising the step, following the scratching steps, of massaging the scratched lines with an antibacterial preparation.

7. The method recited in claim 6, wherein the antibacterial preparation comprises a topical cream comprising neomycin and polymyxin B.

8. The method recited in claim 6, further comprising the step, prior to the massaging step, of cleaning the scratched lines.

9. A noninvasive method of tightening the skin of a patient, the method comprising the steps of:

providing a skin scratching tool comprising:
a handle having a first end and a second end;
a pair of spaced-apart support members, each affixed at a first end adjacent and generally perpendicular to the second end of the handle; and
a plurality of spaced-apart generally parallel blades affixed to, spanning, and generally perpendicular to the support members, the blades each having a sharp side, the sharp sides facing a same direction, the blades further having a predetermined separation between adjacent blades;

selecting a target line in the skin of the patient;

holding the first end of the handle tool;

scratching a first series of lines in the skin parallel to and on a first side of the target line using the scratching tool;

scratching a second series of lines in the skin parallel to and on a second side of the target line using the scratching tool; and permitting the scratches in the skin to heal, during which the skin is tightened.

10. The method recited in claim 9, further comprising the step, following the scratching steps, of massaging the scratched lines with an antibacterial preparation.

11. The method recited in claim 10, wherein the antibacterial preparation comprises a topical cream comprising neomycin and polymyxin B.

12. The method recited in claim 10, further comprising the step, prior to the massaging step, of cleaning the scratched lines.

* * * * *